United States Patent
Krill et al.

(10) Patent No.: US 6,417,406 B1
(45) Date of Patent: Jul. 9, 2002

(54) PROCESS FOR THE PRODUCTION OF 6-METHYL HEPTANONE

(75) Inventors: Steffen Krill, Hanau; Klaus Huthmacher, Gelnhausen, both of (DE)

(73) Assignee: Degussa AG, Duesseldorf (DE)

( * ) Notice: Subject to any disclaimer, the term of this patent is extended or adjusted under 35 U.S.C. 154(b) by 0 days.

(21) Appl. No.: 09/948,650

(22) Filed: Sep. 10, 2001

(30) Foreign Application Priority Data

Sep. 8, 2000 (DE) .......................................... 100 44 390

(51) Int. Cl.$^7$ ................................................ C07C 45/73
(52) U.S. Cl. ........................ 568/388; 568/390; 568/392; 568/396
(58) Field of Search ................................ 568/388, 390, 568/392, 396

(56) References Cited

U.S. PATENT DOCUMENTS 2,499,172 A 2/1950 Smith
4,005,147 A * 1/1977 Fischer et al.
5,840,992 A * 11/1998 Kido et al.
5,955,636 A * 9/1999 Kido et al.

FOREIGN PATENT DOCUMENTS

EP 0 765 853 4/1997

OTHER PUBLICATIONS

B. Zupancic, et al., Synthesis, vol. 11, pp. 913–915, "Aromatic α,β–Unsaturated Nitriles via Polyethelene Glycol–Catalyzed Two–Phase Aldol–Type Condensation", Nov. 1981.

* cited by examiner

*Primary Examiner*—Johann Richter
*Assistant Examiner*—Sikarl A. Witherspoon
(74) *Attorney, Agent, or Firm*—Oblon, Spivak, McClelland, Maier & Neustadt, P.C.

(57) ABSTRACT

The present invention provides a process for producing 6-methyl heptanone and corresponding methyl ketones, in particular phytone and tetrahydrogeranyl acetone, by aldolization of aldehydes with acetone in the presence of an aldolization catalyst and a heterogeneous hydrogenation catalyst containing a polyhydric alcohol.

30 Claims, No Drawings

PROCESS FOR THE PRODUCTION OF 6-METHYL HEPTANONE

CROSS-REFERENCE TO A RELATED APPLICATION

The present application claims priority to German Application No. DE 100 44 390.7 filed Sep. 08, 2000, the contents of which are incorporated herein by reference

BACKGROUND OF THE INVENTION

1. Field of the Invention

The present invention relates to a process for producing 6-methyl heptanone and corresponding methyl ketones, in particular phytone and tetrahydrogeranyl acetone, by aldolization of aldehydes with acetone in the presence of an aldolization catalyst and a heterogeneous hydrogenation catalyst containing a polyhydric alcohol.

2. Background of the Invention

Methyl ketones, in particular 6-methylheptan-2-one, tetrahydrogeranyl acetone and phytone, are important intermediates and starting materials for the production of odoriferous substances, pharmaceutical products and feedstuff additives (J. Org. Chem., 32 (1967), 177; J. Org. Chem., 28 (1963), 45; Bull. Soc. Chim. Fr. (1955), 1586). Furthermore isophytol is a central structural element in vitamin E synthesis.

The production of methyl ketones, in particular methyl heptanone, has been described in the relevant literature employing various synthesis strategies. For example, isoamyl halides and acetic acid esters may be coupled with one another in a nucleophilic substitution reaction in the presence of stoichiometric amounts of a base (pathway A), the β-ketone ester formed as intermediate is decarboxylated with the elimination of the corresponding alcohol and carbon dioxide. However, this process is not economical due to the disproportionate amount of starting materials required, the amount of $CO_2$ and alcohol produced as byproducts, and the salts that are formed (Wagner et al., "Synthetic Organic Chemistry", 327, John Wiley & Sons, Inc., New York)

Ser. Khim. 5 (1972), 1052). The disadvantage of this method is the complicated production of the methyl heptenone and the need to carry out the synthesis as a multistage process. Other pathways that have been described is the oxidation of 6-methyl-5-hepten-2-ol (pathway C) (Recl. Trav. Chim. Pays Bas, 28, 116 (1909)) or the treatment of the alkenol with phosphoric acid and phosphorus pentoxide (pathway D) (Bull. Soc. Chim. Fr., 1799, (1963)). Both methods are unsuitable for industrial production of methyl heptanone because stoichiometric amounts of the corresponding reagents are consumed, the synthesis of the educt involves a multistage process and is complicated.

A large number of synthesis strategies described previously involve the accessibility of 6-methyl-5-hepten-2-one, from which the corresponding methyl heptanone can be produced efficiently by catalytic hydrogenation as illustrated above (pathway B). It was recognized relatively early on by manufacturers of odoriferous substances, aroma substances and vitamins that 6-methyl-5-hepten-2-one represents a central intermediate from which it is possible to produce various vitamins, such as vitamin E and vitamin A, carotinoids and odoriferous substances. Many of these processes are discussed below.

A multistage process starting from acetone (pathway E) is used industrially involving reacting acetone in the first stage in the presence of basic catalysts in ammonia to form methyl butinol. After Lindlar hydrogenation to form methyl butenol, the latter is reacted with diketene to form an intermediate in situ, which in turn is reacted in a Caroll rearrangement to form methyl heptenone (J. Org. Chem., 23, 153, (1958). It is clear that the large number of stages in the process, the use of diketene and acetylene and the associated stringent safety requirements severely restrict the industrial applicability of the process.

Another process for producing methyl heptenone, which has been described, involves reacting isobutene with formaldehyde and acetone under pressure (pathway F). These process conditions, which necessitate the use of high temperatures and pressures in order to achieve good conversions and selectivities, are associated with high apparatus costs and restrict the applicability of the process (DE 12 59 876, DE 12 68 135, U.S. Pat. No. 3,574,773).

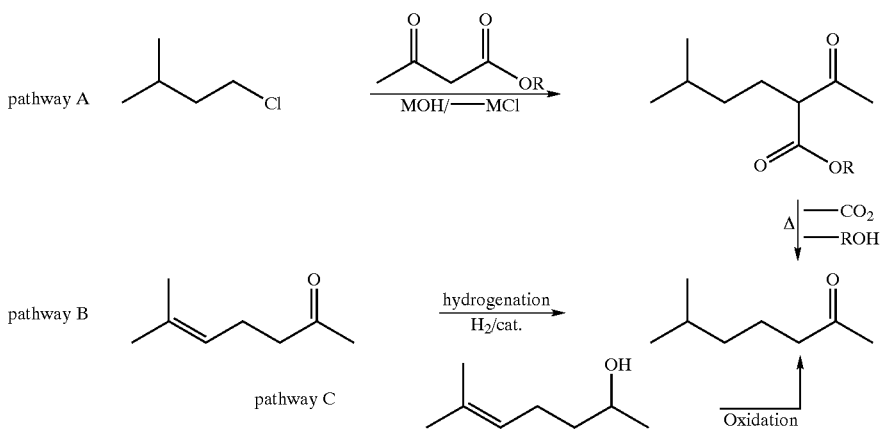

Another synthesis strategy employed starts with the production of various unsaturated methyl heptanone derivatives, such as 6-methyl-5-hepten-2-one or 6-methyl-3,5-heptadien-2-one (pathway B), which are hydrogenated in a separate reaction stage in the presence of heterogeneous catalysts to form methyl heptanone (Izv. Akad. Nauk SSSR, Another described pathway for producing methyl heptenone, which under moderate conditions yields the desired product, is a two-stage process that has been adapted for industrial use. In the first stage isoprene is reacted with gaseous HCl in the presence of a Cu—I halide yielding an isomeric mixture of the corresponding allyl chlorides. The terminal prenyl chloride is coupled with acetone in a two-phase reaction with aqueous sodium hydroxide in the presence of a phase transfer catalyst (pathway G). The disadvantages of this process are the stoichiometric amount of salt that is formed and the moderate yields obtained, approximately 70% (U.S. Pat. No. 3,983,175 and U.S. Pat. No. 3,984,475).

isovaleraldehyde, Example 12), whereby the reaction is carried out at elevated temperatures under hydrogenating conditions (in the presence of hydrogen, preferably at a pressure between 20–30 bar). According to a variant of this process no heterogeneous rare earth oxides are used as aldolization catalysts, but instead a corresponding lipophilic salt (for example stearate) is used. The disadvantage of this

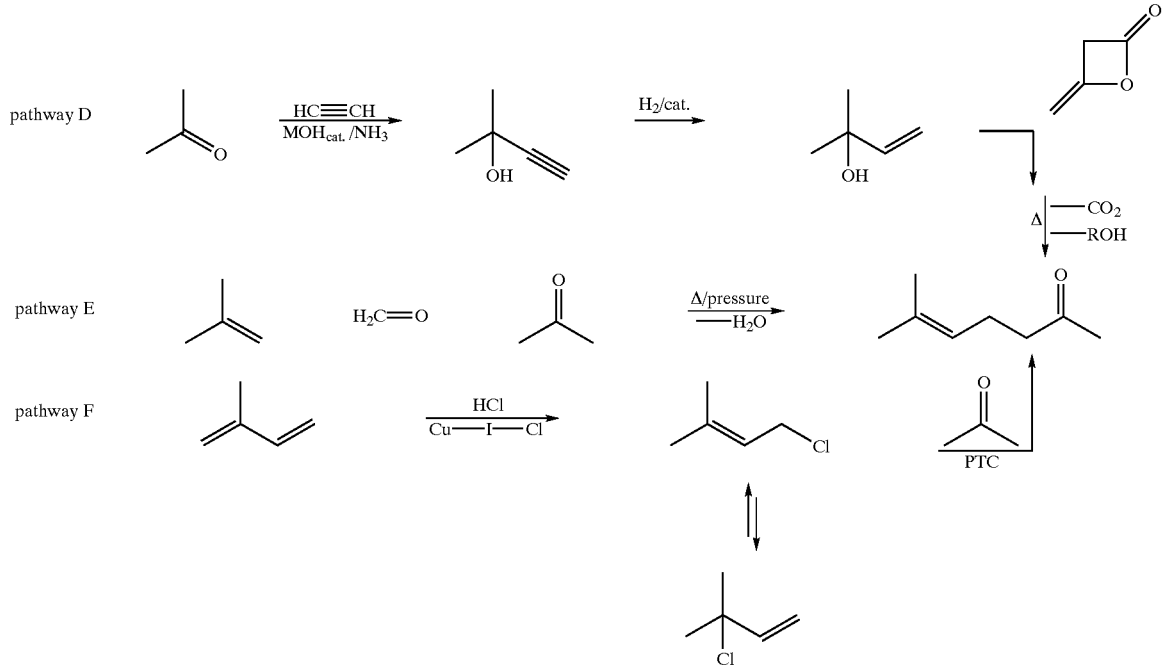

In view of the aforementioned problems, the above-described processes are not useful from an economic standpoint in the synthesis of methyl heptanone. In particular, these processes for producing 6-methyl-heptan-2-one via 6-methyl-5-hepten-2-one are associated with a large number of stages, considerable expenditure and apparatus complexity.

Another described process involves the formation of a double bond isomer of 6-methyl-5-hepten-2-one, namely 6-methyl-3-hepten-2-one, by the cross-aldol condensation at moderate temperatures of isovaleraldehyde and acetone, in the presence of an aqueous alkali compound as catalyst (Nippon Kagaku Kaishi, 59, 224 [1938]).

The relatively low reaction temperatures that are used in order to achieve high selectivities mean that the reaction also stops at the β-hydroxyketone stage (Bull. Soc. Chim. Fr., 112, [1957]).

In GB 1,246, 698 acetone and isovaleraldehyde are reacted together at temperatures of greater than 200° C. and pressures of greater than 30 bar, in which only modest conversions of approximately 25% are achieved and acetone is used in a molar excess of 4 equivalents. In addition to the use of aqueous sodium hydroxide as catalyst for the conversion, heterogeneous oxides are also described as active aldolization catalysts.

DE-OS 26 15 308 (see also U.S. Pat. No. 4,146,581) describes the use of catalytic amounts of rare earth alkaline oxides combined with a heterogeneous hydrogenation catalyst (one or more metals of Group VIII of the Periodic System) for the cross-aldolization of symmetrical ketones with lower aldehydes (see reaction of acetone with process is that to achieve good selectivities, the ketone must be used in a substantial excess (3–5 equivalents with respect to the aldehyde that is used) and the conversion of aldehyde is not complete. With this procedure a considerable amount of unconverted methyl heptenone, in addition to the desired methyl heptanone, is obtained. No details of the effective service life of the heterogeneous systems that are used are given.

DE-OS 26 25 541 (corresponding to U.S. Pat. No. 4,212, 825) is also concerned with a method for the direct production of higher saturated ketones, in particular 6-methyl heptanone, by cross-aldolization of acetone with 3-methyl-butanal using a heterogeneous supported catalyst that contains zinc oxide as aldolization component and nickel, cobalt or copper as hydrogenation component. The disadvantages of this method are incomplete conversions, unsatisfactory hydrogenation yielda, and secondary products that are formed by the consecutive reaction of methyl heptanone with a further equivalent of isovaleraldehyde (product mixture containing 2,10-dimethylundecan-6-one and unsaturated precursors). Moreover, the preparation of the catalyst is complicated. No details are given concerning the long-term activity of the catalyst.

The use of zinc oxide per se as an aldolization catalyst for the production of the corresponding ,β-unsaturated ketones is described in U.S. Pat. No. 4,005,147. The use of lipophilic zinc salts in the presence of a hydrogenation catalyst is described in U.S. Pat. No. Pat. 3,316,303, considerable amounts of the undesired alcohol being formed due to the use of an unsuitable hydrogenation catalyst (sulfide of the elements Mo, Ni, W or a cobalt carbonylation catalyst).

Another method for producing 6-methyl heptanone is described in WO 96/31454, which involves a two-stage process for the cross-aldolization of acetone with isovaleraldehyde in the presence of aqueous sodium hydroxide, this step being performed in the first stage. After obtaining a mixture containing 4-hydroxy-6-methylheptan-2-one, removal of water and hydrogenation are carried out in the presence of a catalytic amount of a Brönsted acid and a heterogeneous noble metal hydrogenation catalyst. It is obvious that this multistage process, in particular the need to change the catalyst environment from a basic to an acidic environment, does not represent a satisfactory solution to the existing problems. In order to achieve high yields, an acetone excess of between 3–5 equivalents with respect to isovaleraldehyde is also employed.

U.S. Pat. No. 5,955,636 describes a process in which the aldolization of isovaleraldehyde with acetone is carried out in the presence of aqueous sodium hydroxide and a heterogeneous noble metal hydrogenation catalyst, wherein the hydrogenation catalyst is suspended in the acetone and at the same time the aqueous sodium hydroxide as well as isovaleraldehyde are added at elevated temperatures to this suspension. The disadvantage of this process is the complicated technical equipment that has to be used for the simultaneous metering in the two solutions. After the reaction the heterogeneous hydrogenation catalyst has to be removed by filtration, followed by phase separation; the upper phase containing the valuable product 6-methyl heptanone and the lower phase containing the aqueous sodium hydroxide diluted by water of reaction. The conversions that can be achieved by this process are approximately 97–98%, while the yields with respect to isovaleraldehyde are approximately 87%. Another disadvantage of this process is the need to separate the fine suspension catalyst before working-up the product, and to separate the noble metal catalyst from the filtration aid in order to recycle the catalyst. These additional steps represents a considerable effort and expenditure in the work-up of the product. The hydrogenation catalyst is distributed between the two phases obtained after the reaction is complete and therefore has to be removed by filtration before the isolation of the organic valuable product. No details are given concerning the recycling and/or reactivation of the aqueous catalyst phase that contains the alkaline aldolization catalyst as well as the heterogeneous hydrogenation catalyst.

With the processes described previously, complete conversion is not normally targeted result because the selectivity of the aldolization decreases with increasing conversion. This decrease in selectivity can be attributed to consecutive reactions of the methyl heptanone that is formed with further equivalents of isovaleraldehyde or to reactions involving one of the intermediates β-hydroxyketone or methyl heptenone.

Another significant disadvantage of the above-described processes is the need to employ large excesses of acetone to achieve high selectivities with respect to isovaleraldehyde. However, acetone tends to dimerize to form mesityl oxide under the specified conditions, which can be detected under hydrogenating conditions as methyl isobutyl ketone. With the processes described in the prior art this homoaldolization of acetone constitutes a substantial secondary reaction that considerably reduces the selectivity as it relates to acetone and which is manifested in a high specific consumption of the ketone.

In particular, all the above-described processes do not consider how the catalyst phase, in particular the hydrogenation catalyst that determines the overall economy of the process, can be recycled. The described processes, which envisage a filtration separation of the suspension catalyst, are unsatisfactory since the catalyst that is filtered off can be separated again only with difficulty from the filter and/or from the filtration aid.

Thus, prior to the present invention no economical processes were known that can be used for the production of methyl ketones, in particular 6-methylheptan-2-one, in which satisfactory yields are obtained with complete conversions (conversions>99%), and in which the catalyst phase containing the aldolization catalyst and the suspended hydrogenation catalyst can be reused without having to employ complicated technical procedures such as filtration. Moreover, prior to the present invention, it has not been possible to find a satisfactory process in order to suppress the undesirable formation of byproducts due to the dimerization of acetone to mesityl oxide and thereby reduce the specific acetone consumption.

SUMMARY OF THE INVENTION

Accordingly, an object of the invention was to find a process for the production of methyl ketones by cross-aldolization of acetone with the corresponding aldehydes under hydrogenation conditions that a.) enables the corresponding methyl ketones to be produced in good yields and high purities with complete conversion (>99%) of the aldehyde used;

b.) avoids the complicated process procedures, e.g., simultaneous addition of both the aqueous alkali solution and the aldehyde;

c.) permits the recycling of the catalyst phase containing the active hydrogenation catalyst and the alkaline aldolization catalyst in a technically simple manner and avoids the complicated filtration of the hydrogenation catalyst;

d.) enables constant, stable yields and process conditions to be ensured with repeated use of the reactivated catalyst phase;

e.) provides a stable catalyst phase that tolerates high levels of secondary products of the reaction, without significant changes in the performance profile (conversion, yield, selectivity, reaction time, etc.), and enables the acetone dimerization as an undesirable secondary reaction to be suppressed and/or reduced.

Accordingly, the present invention provides an improved process for preparing methyl ketones of the formula (1):

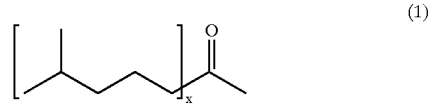

wherein x is a number from 1 to 3, which involves the reaction of an aldehyde of the formula (2):

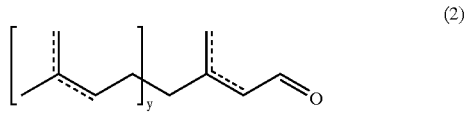

wherein y is from 0 to 2 and the - - - - represents olefinic double bonds with a catalytic suspension, where the catalytic suspension containing a hydrogenation catalyst and an aldolization catalyst suspended in polyhydric alcohol, and the reaction is performed in the presence of hydrogen and acetone.

In one embodiment of the invention the aldolization catalyst and the hydrogenation catalyst are dissolved and/or suspended in the dihydric alcohol or polyhydric alcohol, preferably the polyhydric alcohol is glycerol.

In another embodiment, the catalyst phase together with acetone is placed as a two-phase mixture under hydrogen in an autoclave, and the corresponding aldehyde is pumped in at temperatures of from 40° C. to 200° C. while stirring thoroughly.

In another embodiment, after the end of the reaction the upper phase containing the valuable product (i.e. the corresponding methyl ketone in addition to unreacted acetone) is removed from the glycerol phase, acetone is recovered by distillation, and the corresponding methyl ketone is isolated.

In another embodiment, after the end of the reaction the lower phase containing the catalysts may be concentrated, preferably by evaporation to adjust to the desired water concentration by removing water of reaction, and after replenishing the spent aldolization catalyst is reactivated and used for a new cycle.

DETAILED DESCRIPTION OF THE INVENTION

The invention is a process for the production of methyl ketones of the general formula (1)

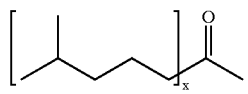
(1)

wherein x denotes a number between 1–3 (for x=1→6-methylheptan-2-one; for x=2→tetrahydrogeranyl acetone; for x=3→phytone)
by reacting hydrogen, acetone and an aldehyde of the general formula (2)

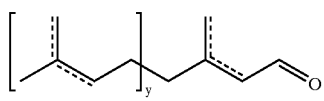
(2)

wherein y denotes a number between 0–2 and the dotted lines in each case represent olefinic double bonds, characterized in that the reaction of the components is carried out in the presence of a polyhydric alcohol that separates from the aldehyde of the formula (2) the catalyst suspension contains the suspended heterogeneous hydrogenation catalyst and the dissolved, alkaline aldolization catalyst, and the catalyst suspension is used after the end of the reaction for further reaction cycles.

It has been found that by using polyhydric alcohols, in particular glycerol, as matrix for two catalyst systems, a significantly simplified reaction procedure is possible. This procedure places the catalyst phase (hydrogenation catalyst and aldolization catalyst) together with acetone in a reaction vessel and the aldehyde component is simply metered into this suspension. The formation of secondary products due to acetone dimerization can be significantly reduced by this measure, whereby the specific consumption of acetone is drastically reduced and the work-up of the product is simplified.

In particular an improved process is described for the production of unsymmetrically substituted ketones that carry an -methyl group, hereinafter termed methyl ketones, by reacting the corresponding aldehydes with acetone under hydrogenation, dehydration and aldolization conditions, wherein the educts that are used and the resultant products are only slightly soluble in the catalyst phase containing both the hydrogenation catalyst and also the alkaline dehydration catalyst and aldolization catalyst.

A further aspect of the invention is a two-phase reaction procedure employing polyhydric alcohol as a suspension agent for the heterogeneous hydrogenation catalyst and the separation of the product phase from the active catalyst phase after phase separation, and the recycling of the catalyst phase.

In the following diagram the reaction is outlined by the example of the acetonization of 3-methylbutyraldehyde (isovaleraldehyde) with the production of methyl heptanone. The compounds in brackets serve as intermediates:

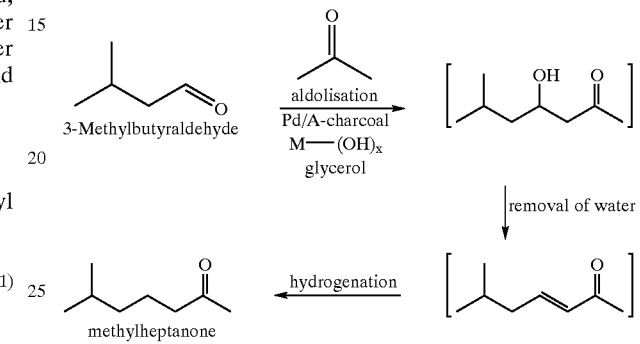

The expression catalyst phase is understood here to denote a phase that contains the aldolization catalyst and the hydrogenation catalyst.

The process according to the invention considerably. simplifies the process procedure compared to those described previously, because the addition of only one component is necessary in order to achieve high selectivities.

Due to the homogeneous distribution of the suspended hydrogenation catalyst in the polyhydric alcohol, after the end of the reaction a defined phase boundary is formed between the product phase and catalyst phase, so that a distribution of the catalyst between the phases (as is the case when using aqueous alkali solutions) is effectively prevented. Separation of the hydrogenation catalyst thus avoids the problems of the earlier process whereby significant procedures must be performed. The separation of catalyst phase and product phase takes place in the simplest case by simply decanting the product phase from the catalyst phase. The catalyst phase that is obtained contains predominantly the water of reaction formed by the condensation, which considerably facilitates the distillative work-up of the organic product phase by the avoidance of azeotropic mixtures between the water and the carbonyl compounds that are present. The catalyst phase contains the active hydrogenation catalyst in the form of the homogeneously distributed suspension and the unconsumed alkaline aldolization catalyst. The adjustment of the water content of the catalyst phase provided for the recycling is carried out any appropriate means, preferably by the water content is adjusted evaporative concentration. Before the glycerol phase is reused, it can be simply replenished with the amount of alkali consumed by secondary reactions.

The process according to the invention thus provides an industrial one reaction vessel procedure for producing methyl ketones, in which the catalyst phase can be completely recycled after carrying out the reaction and phase separation. The reaction procedure includes the addition of the aldehyde to the two-phase mixture of catalyst phase and acetone, which involves a small expenditure as it relates to control procedures. Therefore, the present invention provides a reliable process procedure, because any heat generated from the reaction is simply dissipated by interrupting or slowing down the metering in of the aldehyde.

The work-up or purification of the product takes place without the need to separate the heterogeneous hydrogenation catalyst.

One aspect of the invention relates to a process for the production of methyl ketones, in particular 6-methylheptan-2-one, by production from the corresponding carbonyl compound and acetone, characterized in that both the alkaline condensation catalyst as well as the heterogeneous hydrogenation catalyst are dissolved and/or suspended in a polyhydric, lipophobic alcohol, and the reaction is carried out as a two-phase reaction. In one embodiment, the catalyst-containing lipophobic alcohol phase and acetone are placed in an autoclave under a moderate hydrogen pressure and the aldehyde component is metered in to the two-phase mixture containing acetone and catalyst phase.

This latter embodiment is described below in an example of reacting acetone with isovaleraldehyde to produce 6-methylheptan-2-one. The reaction proceeds in situ via the aldolization stage yielding the corresponding β-hydroxyketone, which is not isolated. Under the reaction conditions elimination of water takes place with the formation of 6-methylhept-3-en-2-one, which is selectively hydrogenated by the homogeneously distributed hydrogenation catalyst in the lipophobic alcohol phase to form the corresponding methyl ketone.

The molar ratio of aldehyde, preferably isovaleraldehyde, to acetone may vary for the reaction, though preferably acetone is used in excess to achieve high product selectivity with regard to the aldehyde, preferably isovaleraldehyde, and a high aldehyde conversion. Good results are obtained if a molar ratio of aldehyde, preferably isovaleraldehyde, to acetone is from 1:0.5 to 1:10, preferably from 1:1 to 1:5.

Basic compounds can be used as aldolization catalysts for the cross-aldolization. Suitable basic compounds include, for example, hydroxides and carbonates of alkali and alkaline earth compounds of the elements lithium, sodium, potassium, magnesium, calcium or barium. Preferred are sodium hydroxide and potassium hydroxide as well as barium hydroxide and calcium hydroxide because they are readily available. Other components may also be used as long as a good solubility in the matrix of the catalyst phase is assured. The production of the catalyst phase is carried out in a simple manner by dissolving the corresponding bases and, if necessary, while heating. According to another embodiment of the invention, the salts are dissolved in the form of their aqueous solutions in the polyhydric alcohol. It is also possible to use mixtures of different stoichiometric amounts of the aforementioned compounds as the aldolization catalyst.

Alcoholates of lower alcohols that are readily soluble in the polyhydric alcohol may also be used as catalyst for the aldolization. By way of example there may be mentioned from these classes of substances methanolates, ethanolates, isopropanolates, butanolates and corresponding branched compounds and homologues. It should however be pointed out that the use of the corresponding alcoholates does not offer any significant advantages compared for example to the convenient and readily available hydroxides. Since water is formed by the in situ reaction, the alcoholates are converted into the corresponding metal hydroxides with the formation of the various alcohols. Amides too effectively catalyze the reaction.

The concentration of the alkaline aldolization catalysts may be varied within wide ranges, a concentration of from 0.1 to 20 mole % of the corresponding base being used in order to achieve good space-time yields and selectivities with regard to the aldehyde that is employed. A concentration of from 0.5 to 10 mole % is preferred.

The concentration of the base in the polyhydric alcohol may be adjusted to from 0.01 wt. % to 20 wt. %. Preferably, the concentration is from 0.1 to 5 wt. %. range, which permits good yields and conversions to be achieved.

The polyhydric alcohol, in particular glycerol or another sugar alcohol, may be used in a volume ratio of alcohol to acetone of from 1:20 to 20:1 with respect to the acetone that is used, a volume ratio of from 1:5 to 5:1 is preferred. Using larger volumes of the catalyst phase is of course possible, though this is at the expense of the space-time yield of the reaction and is therefore undesirable. Although a reduction of the volume of the catalyst phase still leads to satisfactory results, it does not offer any further advantages.

"Polyhydric alcohols" as used include sugar alcohols with a hydrocarbon skeleton of 3–6 carbon atoms, in particular glycerol, though other dihydric to hexahydric alcohols may also be used. Examples of such polyhydric alcohols include ethylene glycol, propanediol, butanediol, glycerol, erythritol and isomeric tetrahydric alcohols, pentaerythritol, various pentahydric alcohols such as arabitol and xylitol, hexahydric alcohols, and polyhydric alcohols not derived from sugar alcohols, such as inositol, as well as related compounds, isomers and homologues.

The reaction may be conducted at temperatures of from 20° C. to 200° C., temperatures of from 80° C. to 140° C. are preferred to achieve high product selectivities and sufficient reaction rates. It is also possible to allow the various successive reactions to proceed in various temperature stages. Thus, at the beg inning of the reaction the selective cross-aldolization may take place at lower temperatures than the following elimination of water to form the, β-unsaturated methyl ketone and its hydrogenation to the saturated methyl ketone.

The process of the invention may be carried out batchwise. According to a batchwise procedure, the polyhydric alcohol phase, which contains the binary catalyst system is placed together with acetone in a pressurized vessel while stirring thoroughly, the desired hydrogen pressure is adjusted, and the contents are brought to the reaction temperature. The corresponding aldehyde, in particular isovaleraldehyde, is then metered in. It is also possible to place only the catalyst phase in the vessel and then to add the mixture of acetone and isovaleraldehyde. Due to selectivity the first variant is preferred, which is attributed to the effective suppression of a homoaldol condensation of isovaleraldehyde with itself when acetone is added to the vessel the stationary ratio between acetone and isovaleraldehyde is always correspondingly sufficiently large.

The present process may also be performed as a two-phase reaction. However, such a react ion requires more apparatus. In this reaction, the polyhydric alcohol phase, which contains only the suspended hydrogenation catalyst, is placed together with acetone in the re action vessel under the desired hydrogen pressure and at the reaction temperature, and both the aldehyde as well as an aqueous solution of the aldolization catalyst are then metered in.

In another embodiment, the process is operated continuously, the catalyst phase and educts being brought into contact with one another, optionally countercurrently. After the reaction, the phases are separated, the polyhydric alcohol phase is recycled continuously to the reactor. The replenishment of spent catalyst and replenishment of the educts also takes place at this stage before recycling to the reactor.

For a better control of the reaction, in particular for a better temperature control in order to dissipate the heat of reaction, solvents inert under the reaction conditions that do not influence the selectivity may be employed. However, in the above-described two-phase reaction, a solvent is not absolutely necessary, and preferably, the reaction is carried out in the absence of a solvent in order to achieve high volume yields. Example of such solvents include, for example, aliphatic hydrocarbons such as pentane, hexane, heptane, octane and branched homologues, or aromatic hydrocarbons such as benzene, toluene, xylene, or ethers such as diethyl ether, dibutyl ether, tetrahydrofuran, dioxane, glymes, diglymes and corresponding derivatives, as well as alcohols such as methanol, ethanol, propanol, butanol and branched homologues and derivatives of the aforementioned compounds. Also suitable as solvents within the context of the invention are higher aliphatic ketones that have a lower solubility in the glycerol phase than acetone itself. Examples of such ketones that may be mentioned include diethyl ketone, methyl ethyl ketone, diisopropyl ketone, dibutyl ketone and, in particular, methyl isobutyl ketone, the latter preferably being used as solvent for the reaction since it constitutes a byproduct of the reaction that is derived from the self-aldolization of acetone.

The hydrogenation catalysts used may be easily accessible supported metal catalyst that have been commercially developed as hydrogenation catalyst. Examples of suitable metals that have good selectivities and lifetimes are palladium, platinum, rhodium and nickel, which may be used in the form of the elements, oxides and mixed oxides with other metals, or as alloys with other metals. Suitable supports are activated charcoal, aluminum oxide, silicon dioxide and other commercially available catalyst supports known in the art.

The amount of these hydrogenation catalysts that is used is from 0.01 wt. % to 5 wt. %, preferably from 0.1 wt. % to 1 wt. %.

The hydrogen pressure that is employed may vary and is not restricted, although preferably good results are obtained at pressures of from 1 to 40 bar. Higher pressures may also be employed, but are not desirable because of the burden placed on the apparatus. A preferred pressure range is from 5 to 20 bar.

Another aspect of the present invention is the work-up of the two-phase reaction mixture, which includes isolating the product, recycling unreacted educts, and, of particular importance, conditioning the catalyst phase before use in a new reaction cycle.

After the reaction is complete a two-phase reaction mixture is obtained that contains the active catalyst phase and of the product phase. The water formed in the dehydration of the β-hydroxyketone that is present in situ dissolves essentially in the glycerol phase and is separated from the product by extraction in the catalyst phase. The suspended hydrogenation catalyst is distributed homogeneously in the polyhydric alcohol phase (flotation and distribution of the hydrogenation catalyst between the phases is effectively suppressed by the use of polyhydric alcohols as a catalyst matrix).

The product phase and catalyst phase, which form sharp phase boundaries, are separated from one another by, in the simplest case, removing the supernatant product phase. The catalyst phase contains substantially glycerol, water, the metal salt of the carboxylate formed by a Cannizarro reaction and corresponding to the aldehyde that is employed (if isovaleraldehyde and NaOH are used, sodium isovalerate is formed), the aldolization catalyst and the heterogeneous hydrogenation catalyst.

The process is characterized by the significant amounts of secondary products of the reaction, in particular the carboxylate salts formed by the Cannizarro reaction, are tolerated without any significant effects being observed on the selectivity and yield. After the consumed aldolization base is replenished the catalyst phase can be recycled without any restrictions.

The recycled catalyst phase is characterized, in addition to the carboxylate salts that are present, also by its water content. The carboxylate concentration is conventionally from 0.1 to 70 wt. %, and the water content is adjusted to from 0.1 to 50 wt. %. Tto achieve good yields and to reduce the necessary discharge rate, a carboxylate content of from 10 to 30 wt. % is preferred. The water content of the recycled glycerol phase is preferably adjusted to from 1 to 10 wt. % in relation to the polyhydric alcohol. The sodium hydroxide concentration in the catalyst phase is within certain limits not critical for the reaction and is may be adjusted to from 0.01 wt. % to 20 wt. %. A preferred concentration range is from 0.1 to 5 wt. %.

The adjustment of the water concentration before the recycling of the catalyst phase is achieved in the simplest case by simple evaporative concentration of the glycerol phase, a two-phase mixture being obtained as a distillate. The organic phase consists of unreacted acetone and relatively small amounts of methyl isobutyl ketone. The aqueous phase may be discarded, or may be worked-up further. Replenishment of the basic aldolization catalyst is carried out by addition in bulk, or in the form of the corresponding solutions of the bases in suitable solvents. Solvents may include either the polyhydric alcohol itself, or also lower alcohols with 1–6 carbon atoms, or even water.

The purity of the methyl ketones isolated by the process according to the invention, in particular the purity of the 6-methylheptan-2-one, which can be obtained by reacting acetone with isovaleraldehyde, corresponds to a product quality such as is required for use as an educt for the synthesis of intermediates for the synthesis of vitamin E, vitamin A and various carotinoids.

Having generally described this invention, a further understanding can be obtained by reference to certain specific examples which are provided herein for purposes of illustration only, and are not intended to be limiting unless otherwise specified.

EXAMPLES

Example 1

Two-phase Aldolization of Isovaleraldehyde and Acetone with Glycerolic NaOH 250 grams (g) of glycerol (anhydrous, superpure, from Merck), and 6 g of hydrogenation catalyst (Pd on charcoal, 5 wt. %, E 101 R/W Degussa AG, $H_2O$ content 53.9%) are placed in a 2 liter (l) autoclave equipped with a mechanical stirrer, and 4 g of NaOH (0.1 mole, 2.06 mole % with respect to isovaleraldehyde) are added thereto while heating. After the NaOH has completely dissolved 436 g (7.5 moles) of acetone are added to this suspension. The two-phase mixture is heated to 120° C. and a hydrogen pressure of 15 bar is adjusted in the autoclave. 430.7 g of isovaleraldehyde (4.85 moles) from a receiver are added to this mixture through a dipping tube using an HPLC pump. The molar ratio of aldehyde to acetone is thereby 1:1.55. The metering time is 3 hours (h), and the reaction temperature is maintained between 120° C.–125° C. After the end of the addition the reaction mixture is stirred for a further hour under hydrogen pressure.

After the reaction mixture has cooled to room temperature the autoclave is opened and the two-phase mixture is separated. In the upper phase containing the product the yield is determined by means of quantitative gas chromatography with n-dodecane as internal standard. The quantitative determination gave 558.1 g of 6-methyl heptanone (4.35 moles), which corresponds to a yield of 89.7%. The isovaleraldehyde conversion is 98.9%.

Example 2
Recycling of the Glycerol Catalyst Phase

The same procedure as in Example 1 is employed, identical amounts of starting substances being used, and the catalyst phase formed after the phase separation is recycled, in which first of all the unconsumed residual catalyst concentration (NaOH) and the amount of sodium salt of isovaleric acid formed by the catalyst consumption are analytically determined. The depleted aldolization catalyst is replenished in order to restore the original concentration. The replenishment of the aldolization catalyst (NaOH) is carried out by adding the catalyst as a 50% $NaOH-H_2O$ solution. The concentration of NaOH in each batch is 2.06 mole % with respect to isovaleraldehyde. The hydrogenation catalyst is not replenished.

After the end of the reaction, phase separation and replenishment of the base, the catalyst suspension is concentrated by evaporation on a rotary evaporator, a two-phase distillate being formed. The lower, aqueous phase is discarded, while the upper, organic phase is combined with the organic product phase and is worked-up by distillation.

From Table I of this recycling series it is clear that stable yields (89–92%) and conversions (99%–>99%) can be obtained according to the afore-described procedure with repeated recycling of the catalyst phase.

TABLE I

| Cycle No. | Yield | Conversion | Selectivity |
| --- | --- | --- | --- |
| 0 | 88.5 | 97.8 | 90.5 |
| 1 | 91.8 | 99.2 | 92.5 |
| 2 | 90.5 | 99 | 91.4 |
| 3 | 91 | 99 | 91.9 |
| 4 | 92 | 98.7 | 93.2 |
| 5 | 91.3 | 99.4 | 91.85 |

Example 3
Recycling of the Glycerol Catalyst Phase with Higher Catalyst Concentration with Continuous Raising of the Carboxylate Level of the Catalyst Phase The same procedure as described in Example 2 is employed, identical amounts of starting substances being used and the catalyst phase formed after the phase separation being recycled, in which first of all the unconsumed residual catalyst concentration (NaOH) and the amount of the sodium salt of isovaleric acid formed by the catalyst consumption are analytically determined and the depleted catalyst is replenished in order to restore the original concentration.

The replenishment of the aldolization catalyst (NaOH) is carried out by addition as a 50% NaOH solution. The concentration of NaOH in each batch is 3.09 mole % with respect to isovaleraldehyde. This corresponds to an NaOH amount of 6 g (0.15 mole) per batch. The mass of the catalyst phase is increased per batch due to the formation of the sodium salt of 3-methylbutyric acid. The hydrogenation catalyst is not replenished.

After the end of the reaction, phase separation and replenishment of the base, the catalyst suspension is concentrated by evaporation on a rotary evaporator, a two-phase distillate being formed. The lower, aqueous phase is discarded, and the upper, organic phase is combined with the organic product phase and worked-up by distillation.

TABLE II

| Cycle No. | Yield [%] | Conversion [%] | Selectivity [%] | Na Carboxylate [wt. %] |
| --- | --- | --- | --- | --- |
| 0 | 90.7 | 99.8 | 90.9 | 0 |
| 1 | 91.2 | 99.7 | 91.5 | 6.3 |
| 2 | 91.6 | 100 | 91.6 | 12.3 |
| 3 | 91.2 | 99.9 | 91.3 | 17.5 |
| 4 | 91.8 | 98.8 | 92 | 23.0 |
| 5 | 92.5 | 100 | 92.5 | 28.7 |

From Table II it is clear that stable yields of ca. 91% and complete conversions are obtained according to the afore-described procedure, under repeated recycling of the catalyst phase. It is also clear that an increasing amount of sodium salt due to the recycling does not have any noticeable effects on the activity of the catalyst phase.

Example 4
Aldolization of Isovaleraldehyde and Acetone with Glycerolic NaOH 350 g of glycerol (anhydrous, superpure, from Merck) and 6 g of hydrogenation catalyst (Pd on charcoal, 5 wt. %, E 101 R/W Degussa AG, $H_2O$ content 53.9%) are placed in a 2 l autoclave equipped with a mechanical stirrer and 6 g NaOH (0.15 mole, 3.02 mole % with respect to isovaleraldehyde) are added thereto while heating. After the NaOH has completely dissolved, 436 g (7.5 mole) of acetone are added to this suspension. The two-phase mixture is heated to 120° C. and a hydrogen pressure of 15 bar is established in the autoclave. 431.0 g of isovaleraldehyde (4.96 mole according to gas chromatography quantitative determination) from a container are metered in to this mixture through a dipping tube using an HPLC pump. The molar ratio of aldehyde to acetone is thus 1:1.51. The metering time is 3 hours, and the reaction temperature is maintained between 120° C.–130° C. After the end of the addition the contents are stirred for a further hour under hydrogen pressure.

After the reaction mixture has cooled to room temperature the autoclave is opened and the two-phase mixture is separated. The yield is determined in the upper, product-containing phase by means of quantitative gas chromatography using n-dodecane as internal standard. The quantitative determination gave 589.9 g of 6-methylheptan-2-one (4.70 moles), corresponding to a yield of 92.6%. The isovaleraldehyde conversion is 99.8%.

According to quantitative determination of the organic product phase that is obtained, 0.21 mole of methyl isobutyl ketone (MIBK) is detected, which means that 0.42 mole of acetone has reacted under dimerization. This corresponds to a MIBK selectivity of 5.6% with respect to acetone.

Comparative Example 1
Aldolization of Isovaleraldehyde and Acetone with Aqueous NaOH 350 g of water and 6 g of hydrogenation catalyst (Pd on charcoal, 5 wt. %, E 101 R/W Degussa AG, $H_2O$ content 53.9%) are placed in a 2 l autoclave equipped with a mechanical stirrer and 6 g of NaOH (0.15 mole, 3.02 mole % with respect to isovaleraldehyde) are added thereto while heating. 436 g (7.5 mole) of acetone are added to this suspension at room temperature. The suspension is heated to 120° C. and a hydrogen pressure of 15 bar is established in the autoclave. 431.0 g of isovaleraldehyde (4.96 moles according to gas chromatography quantitative determination) from a receiver are added to this mixture through a dipping tube using an HPLC pump. The molar ratio of aldehyde to acetone is thus 1:1.51. The metering time is 3 hours, and the reaction temperature is maintained between 120° C.–130° C. After the end of the addition the reaction mixture is stirred for a further hour under hydrogen pressure.

After cooling to room temperature the autoclave is opened and the two-phase mixture is separated. The heterogeneous hydrogenation catalyst floats on the phase boundary between the aqueous and organic product phases and has to be removed by filtration before the product is worked-up. The yield in the upper, product-containing phase is determined after phase separation by quantitative gas chromatography using n-dodecane as internal standard. The quantitative determination gave 587.7 g of 6-methylheptan-2-one (4.58 mole), corresponding to a yield of 92.4%. The isovaleraldehyde conversion is 99.9%.

According to quantitative determination of the organic product phase that is obtained, 0.55 mole of methyl isobutyl ketone is detected, which means that 1.1 mole of acetone have reacted under dimerization. This corresponds to an MIBK selectivity of 14.7% with respect to acetone.

The Comparative Example shows that when water is used considerable amounts of undesirable MIBK are formed, whereas when glycerol is used the undesirable formation of this byproduct can be suppressed. In other words, the use of glycerolic NaOH catalysts according to the invention can reduce the formation of the byproduct MIBK by at least 50%, and even by more than 60%.

Example 5

Synthesis of methyl heptanone by co-aldolization of acetone with isovaleral using glycerolic solutions of various alkali metal and alkaline earth metal hydroxides Under otherwise identical reaction conditions as described in Example 4, various alkali metal hydroxides and alkaline earth metal hydroxides are used as aldolization catalysts. The results are summarized in the following Table III.

TABLE III

| Type/Conc. of the Catalyst Base* | Yield [%] | Conversion [%] | Selectivity [%] | MIBK** Formation [mole] |
|---|---|---|---|---|
| LiOH [4 mole %] | 92.5 | >99.9 | 92.5 | 0.26 |
| NaOH [4 mole %] | 93.2 | >99.9 | 93.2 | 0.28 |
| KOH [4 mole %] | 94.6 | >99.9 | 94.6 | 0.29 |
| Ca(OH)$_2$ [4 mole %] | 85.4 | 98.6 | 86.6 | 0.02 |

*Concentration with respect to isovaleraldehyde
**MIBK = methyl isobutyl ketoneEMBED Obviously, numerous modifications and variations on the present invention are possible in light of the above teachings. It is therefore to be understood that within the scope of the appended claims, the invention may be practiced otherwise than as specifically described herein.

What is claimed is:
1. A process for producing a methyl ketone of the formula

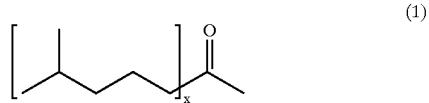

wherein x is a number from 1 to 3, comprising reacting an aldehyde of the formula (2):

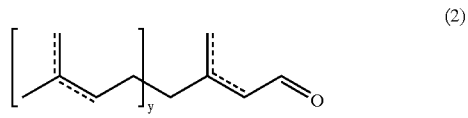

wherein y is from 0 to 2 and the - - - - represents olefinic double bonds with a catalytic suspension, wherein the catalytic suspension comprises a hydrogenation catalyst and an aldolization catalyst suspended in polyhydric alcohol, in the presence of hydrogen and acetone.

2. The process of claim 1, further comprising isolation of the methyl ketone of formula (1) after said reacting.

3. The process of claim 2, wherein said isolation comprises separating a upper phase comprising said methyl ketone and a lower phase comprising said catalytic suspension.

4. The process of claim 3, wherein said after said lower phase is separated from said upper phase, the lower phase comprising the catalytic suspension, is recycled to react with the aldehyde of formula (2) in the presence of hydrogen and acetone.

5. The process of claim 1, wherein x=1.
6. The process of claim 1, wherein x=2.
7. The process of claim 1, wherein x=3.
8. The process of claim 1, wherein said polyhydric alcohol is selected from the group consisting of ethylene glycol, propanediol, butanediol, glycerol, erthritol, isomeric tetrahydric alcohol, pentaerythritol, hexahydric alcohol and pentahydric alcohol.

9. The process of claim 8, wherein said polyhydric alcohol is glycerol.

10. The process of claim 1, wherein said polyhdric alcohol is selected from the group consisting of arabitol, xylitol and inositol polyhydric alcohol.

11. The process of claim 1, wherein the aldolization catalyst is a basic salt of an alkali metal or alkaline earth metal.

12. The process of claim 11, wherein said aldolization catalyst is selected from the group consisting of lithium hydroxide, lithium carbonate, sodium hydroxide, sodium carbonate, potassium hydroxide, potassium carbonate, magnesium hydroxide, magnesium carbonate, calcium hydroxide, calcium carbonate, barium hydroxide, barium carbonate and mixtures thereof.

13. The process of claim 12, wherein said aldolization catalyst is sodium hydroxide.

14. The process of claim 1, wherein said aldolization catalyst is selected from the group consisting of metanolate, ethanolate, isopropaneolate, and butanolate.

15. The process of claim 1, wherein the aldolization catalyst is present in an a mount from 0.1 to 20 mole %.

16. The process of claim 15, wherein the aldolization catalyst is present in an amount from 0.5 to 10 mole %.

17. The process of claim 1, wherein the polyhydric alcohol to acetone ratio is from 1:20 to 20:1.

18. The process of claim 17, wherein the polyhydric to acetone ration is from 1:5 to 5:1.

19. The process of claim 1, wherein the hydrogenation catalyst is selected from the group consisting of palladium, platinum, rhodium, nickel, palladium oxide, platinum oxide, rhodium oxide, nickel oxide and mixtures thereof.

20. The process of claim 1, wherein the hydrogenation catalyst is supported on an inert support selected from the group consisting of activated charcoal, aluminum oxide, and silicon dioxide.

21. The process of claim 1, wherein the hydrogenation catalyst is present in the amount of from 0.01 wt % to 5 wt %.

22. The process of claim 21, wherein the hydrogenation catalyst is present in the amount of from 0.1 wt % to 1 wt %.

23. The process of claim 1, wherein said aldehyde of formula (2) is isovaleraldehyde.

24. The process of claim 1, wherein said reacting is performed under pressure of from 1 to 40 bar.

25. The process of claim 24, wherein said pressure is from 5 to 20 bar.

26. The process of claim 1, wherein said catalyst suspension is mixed with acetone prior to said reacting with the aldehyde of formula (2).

27. The process of claim 1, which is performed at a temperature of from 20 to 200° C.

28. The process of claim 27, which is performed at a temperature of from 80 to 140° C.

29. The process of claim 1, wherein the ratio of the aldehyde to acetone is from 1:0.5 to 1:10.

30. The process of claim 29, wherein the ratio of the aldehyde to acetone is from 1:1 to 1:5.

* * * * *